United States Patent [19]
Grey et al.

[11] Patent Number: 5,246,862
[45] Date of Patent: Sep. 21, 1993

[54] METHOD AND APPARATUS FOR IN-SITU DETECTION AND DETERMINATION OF SOIL CONTAMINANTS

[75] Inventors: Clifford E. Grey; Stafford S. Cooper; Philip G. Malone, all of Vicksburg, Miss.

[73] Assignee: The United States of America as represented by the Secretary of the Army, Washington, D.C.

[21] Appl. No.: 37,754

[22] Filed: Mar. 24, 1993

[51] Int. Cl.⁵ ............ G01N 33/22; G01N 33/24
[52] U.S. Cl. ................... 436/28; 436/164; 436/169; 422/82.07; 422/66; 73/863.23
[58] Field of Search ............... 436/27–31, 436/164, 169; 422/82.05, 82.07–82.11, 66; 73/863.23; 364/420, 498

[56] References Cited

U.S. PATENT DOCUMENTS

| | | | |
|---|---|---|---|
| 2,242,161 | 5/1941 | Athy et al. | 436/28 |
| 4,056,969 | 11/1977 | Barringer | 436/29 |
| 4,659,676 | 4/1987 | Rhyne | 436/27 |
| 4,696,903 | 9/1987 | Owen | 436/28 |
| 5,010,776 | 3/1991 | Lucero et al. | 73/863.23 |
| 5,128,882 | 7/1992 | Cooper et al. | 364/420 |

*Primary Examiner*—Lyle A. Alexander
*Attorney, Agent, or Firm*—Luther A. Marsh

[57] ABSTRACT

A reagent carrying tape is captured between the soil and the outer wall of a penetrometer. As the penetrometer moves with respect to the soil, the tape is pressed against an optical window in the penetrometer. Contaminants in the soil reacting with the reagents cause an optically sensible reaction in the tape to occur which is optically detected at the optical port as the penetrometer moves with respect to the tape and the soil sample. The optically sensible reaction occurring in the tape is optically isolated from the masking effects of the soil. A method is also disclosed.

17 Claims, 3 Drawing Sheets

METHOD AND APPARATUS FOR IN-SITU DETECTION AND DETERMINATION OF SOIL CONTAMINANTS

BACKGROUND OF THE INVENTION

In-situ determination of contaminants in soil has been achieved for those components which could be determined from their fluorescence. Soil contaminants that do not fluoresce are typically determined by recovering a sample and submitting the sample to a laboratory for analysis. Such sampling and analysis has shortcomings in that the sample may be sufficiently disturbed so that an accurate characterization of the contaminant may not be readily achieved.

Where colorimetric techniques have been attempted, the soil color may mask or interfere with the color changes of contaminated species.

Accordingly, a technique is desired which will allow for the detection and determination of soil contaminants on a continuous basis using a colorimetric technique. Also, improvements in fluorescent techniques are desirable.

SUMMARY OF THE INVENTION

The invention is based upon the discovery that detection and determination of the concentration of soil contaminants may be achieved in-situ using a disposable indicator tape and solvents dispensed from a cone penetrometer into the adjacent soil. A remotely read optical instrument incorporated into the cone penetrometer permits the changes in the chemical character of the indicator tape to be determined and recorded without removing the penetrometer from the soil. The invention allows for the determination of chemical contaminants in soil under industrial installations. The invention also allows for the use of colorimetric techniques in soils where the soil color would normally mask the change in the reagent color if the reaction were run directly in the soil. A continuous record may be made of the concentration of contaminants in the soil without retrieving the indicator tape.

In a particular embodiment, the invention comprises an apparatus for in-situ determination of soil contaminants comprising a penetrometer for penetrating the soil. The penetrometer has an inner chamber, an outer soil contacting wall, an interconnecting tape strip channel, and an optical port in the soil contacting wall. An indicator tape strip is mounted in the penetrometer and is threaded between the chamber and the optical port through the tape channel. The tape strip carries a reagent into contact with the soil above the tape strip channel. The tape is deployed by frictional contact with the soil as the penetrometer moves relative to the soil sample. The reagent carried by the tape reacts with the adjacent soil sample for developing an optically sensible reaction in the tape strip. Optical means is coupled to the optical port for optically sensing the reaction in the tape strip as the penetrometer moves relative to the soil sample. A sensor is coupled to the optical means and is responsive to the sensed reaction for producing an electrical signal for characterizing the contaminant.

In one embodiment, the optical means comprises a fiber optic including an illuminating channel carrying radiant energy to the tape surface through the optical port and a receiving channel for receiving reflected energy from the tape and transmitting it to the sensor remotely located from the sample.

In one embodiment, the tape carries a liquid reagent. In another embodiment, the tape carries a solid or semisolid reagent which may be microencapsulated. The reagent may be activated by pressure as the tape is deployed.

In yet another embodiment of the invention, the indicator tape includes a permeable membrane covering at least one surface of the tape in contact with the soil sample during tape deployment for physically excluding soil particles and optically segregating the soil sample color from the optically sensible reaction.

The invention also includes a procedure for determining the changes in the spectral character of an indicator tape using remote sensing. The invention also includes a procedure for injecting or metering a solvent or wetting agent into the soil sample which allows contaminants to be determined in soil samples of different moisture content.

A method has also been provided for sensing contaminants in-situ by isolating the optically sensible reaction between the reagent and the contaminant in a separate medium.

DESCRIPTION OF THE INVENTION

The invention comprises a system for in-situ detection and determination of contaminants in soil samples. The invention is adapted for the determination and measurement of the concentration of chemical contaminants in soil without removing the sample from the ground site.

A system for in-situ detection and measurement of the concentration of chemical contaminants in the soil is disclosed. In general, the invention contemplates the use of an indicator tape, means for placing the tape in contact with the soil and means for optically sensing the reaction of the soil sample with a reagent carried by the tape. The invention also contemplates a technique for wetting the soil with a solvent to allow the contaminants to quickly move into the indicator tape for producing the changes which can be measured optically. In one embodiment, color changes are sensed for characterizing the contaminants. In another embodiment, fluorescence of the contaminants is measured. In yet another embodiment, a fluorescent agent in the tape is quenched by the presence of the contaminating material.

Figure 1:
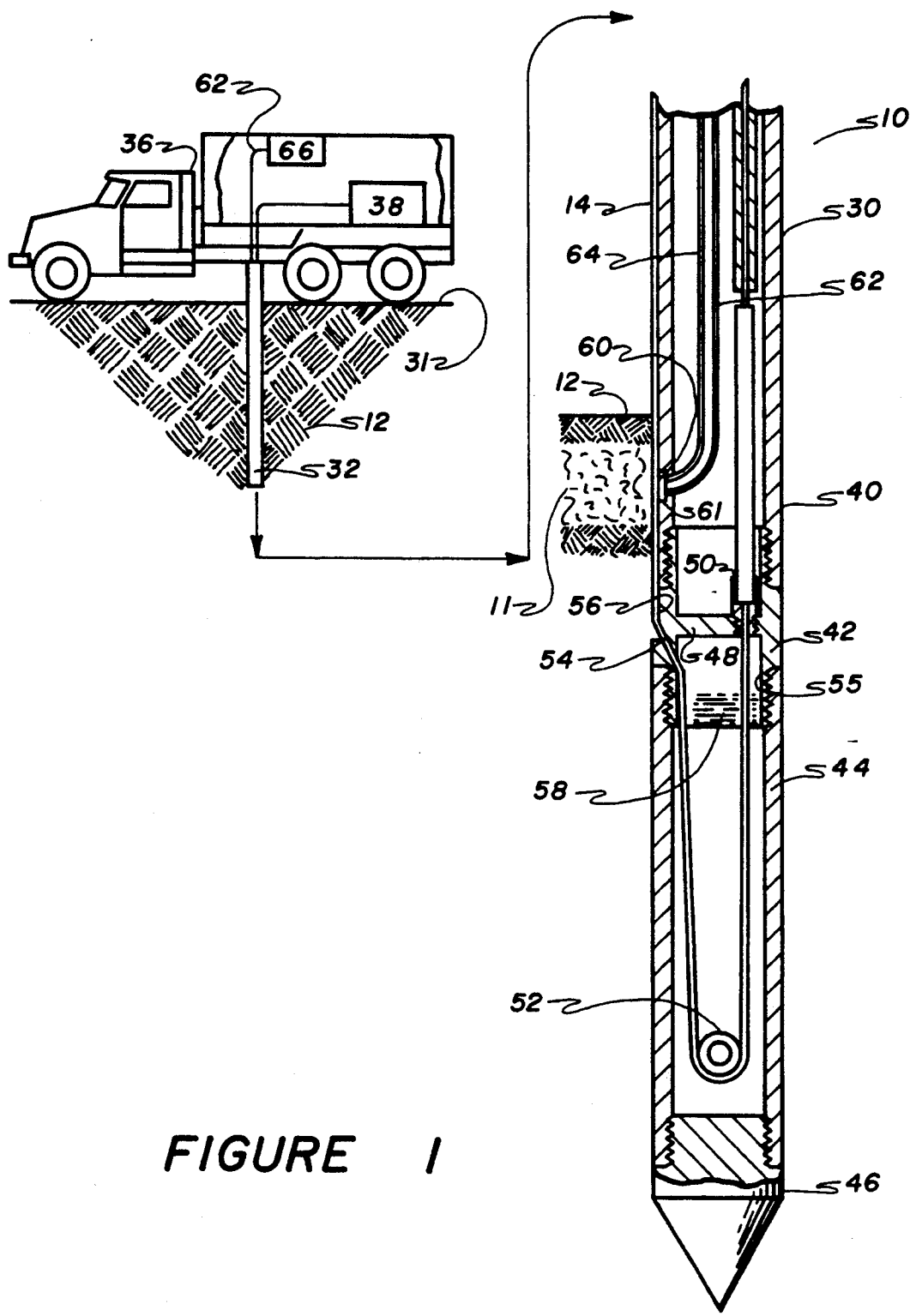
FIG. 1 is a fragmentary, partly enlarged side sectional elevation of an apparatus for in-situ determination of soil contaminants in accordance with the present invention.

In a particular embodiment shown in FIG. 1, the invention comprises a system 10 for sensing contaminants 11 in the soil 12 by means of an indicator tape 14.

Figure 2:
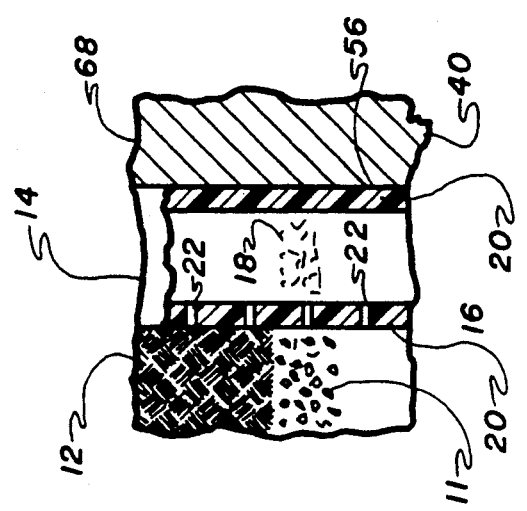
FIG. 2 is a side sectional elevation of an indicator tape in accordance with the present invention.

The tape 14, as illustrated in FIG. 2, comprises a woven or non-woven fabric layer 16 which carries a reagent 18 which may be in liquid, solid or semi-solid form or which, alternatively, may be microencapsulated. The reagent or reagents change the optical properties of the fabric 16 in response to the presence or concentration of specified chemical compounds in the surrounding soil 12. The tape 14 also includes one or more porous outer layers 20. The outer layer 20 has micropores 22 (e.g., 3-6 microns) which allows for the diffusion of contaminants 11 into the fabric 16 for reaction with the reagents 18.

As illustrated in FIG. 1, the tape 14 is carried into contact with the soil 12 by means of a suitable vehicle such as a penetrometer 30. In the arrangement illustrated, the tape 14 is supplied in a continuous strip from a tape feed (not shown) located at the ground surface 31. The penetrometer 30 is connected to the surface 31 by a hollow string 32 of interconnected pipe sections in a known manner. A vehicle 36 which contains the tape supply and other equipment for pushing the penetrometer 30 into the soil 12 also may have a sensing instrument 38 such as, for example, a spectrophotometer or a fluorometer or other suitable instrument for analyzing optical signals.

The tape passes down through the string 32 and an upper steel housing portion 40 of the penetrometer 30. The upper housing 40 is threaded to a bushing 42 for connection to a lower housing 44 and a nose cone 46 for facilitating soil penetration in axial alignment as illustrated. The bushing 42 has an apertured web 48 and a tape guide 50 formed in an aperture in the web 48. The tape 14 is threaded through the tape guide 50 around a pulley (or smooth bearing surface) 52 mounted in the lower housing 44. An external tape guide in the form of a slot 54 is formed in the lower wall 55 of the bushing 42 just below the web 48. The tape 14 is threaded through the slot 54 for communication with the soil 12. As the penetrometer 30 is pushed downwardly in the soil 12, the tape 14 is captured between the external wall 56 of the penetrometer 30 and the soil 12. The tape 14 remains stationary with respect to the soil 12 and is deployed externally of the penetrometer 30 as it moves downwardly in the soil.

The upper housing 40 has an optical port 60 in the form of a quartz or sapphire lens or window formed in the aperture 61. An optical excitation fiber 62 and an optical measurement fiber 64 are each optically coupled to the optical port 60 as shown. The excitation fiber 62 is coupled to a source 66 (e.g. a laser diode) of optical radiation located in the vehicle 36. The wavelength of the optical radiation may range from infrared through the visible and ultraviolet. The measurement fiber 64 is coupled to the instrument 38. Both fibers 62 and 64 pass through the string 32 as illustrated.

The tape 14, which overlies the optical port 60, is captured between the soil 12 and the penetrometer 30. As the penetrometer 30 is pushed into the soil the tape 14 is stationary relative thereto. The optical port 60 moves with respect to the tape 14 so that it may be optically scanned. The lower housing 44 may contain a supply of fluid 58 which is metered or wicked into the soil 12 by the tape 14 as the tape passes through the lower housing 44 towards the slot 54. The fluid 58 may be a reactive reagent, water, or a solvent (e.g., alcohol) for dissolving or wetting the contaminants 11 in the soil 12. In particularly dry soils, for example, the fluid 58 may be water for hydrating the soil 12 adjacent the tape 14.

In an alternate embodiment, the excitation fiber 62 may be replaced by a lamp or other radiant energy source (not shown) situated in the interior of the upper housing so as to pass light through the optical port 60.

In operation, the tape 14 passes through the upper housing 40 and the tape guide 50. The tape 14 is wetted with the solvent 58 as it passes into the lower housing 44 in the reservoir around the tape guide pulley 52. The tape 14 is dispensed through the external tape guide 54 and is captured between the soil 12 and the outer wall 56 of the penetrometer 30 as illustrated. The tape 14 is pressed against the soil 12 and is held in stationary contact by the action by the penetrometer 30 being advanced into the soil 12. The wetted indicator tape 14 reacts with the contaminants 11 present in the soil 12 as they pass through the porous transparent covering 20 of the tape 14. If the solvent 58 is employed, it is metered by surface affinity with the tape 14 or by wicking action. The solvent 58 dissolves or wets contaminants 11 which diffuse into the fabric 16 through the micro-pores 22 for reaction with the reagent 18 causing a change in the color or appearance of the fabric 16 to develop. The change in appearance is indicated by the hatched lines 70 in FIG. 3. As the reaction between the contaminants 11 and the reagent 18 continues, the change in appearance 70 develops and becomes optically sensible.

In accordance with the invention, the optically sensible reaction which occurs in the fabric 16 carrying the reagent 18 may be any one of a number of reactions tailored for a particular contaminant In U.S. Pat. No. 5,128,882, incorporated herein by reference, the spectral characteristics of in-situ soil are examined for sensing contamination in the soil sample itself. In the present invention the spectral characteristics of the reaction product of soil contaminants are examined in an isolated medium, i.e., the tape 14.

The instrument 38 receives the reflected illumination and measures the change in the optical properties of the tape 14. The response of the instrument 38 may be recorded or displayed or both. The quantitative measurement of the contaminants may be made by comparing the in-situ response of the instrument 38 with a controlled sample of a known level of contamination.

Figure 3:
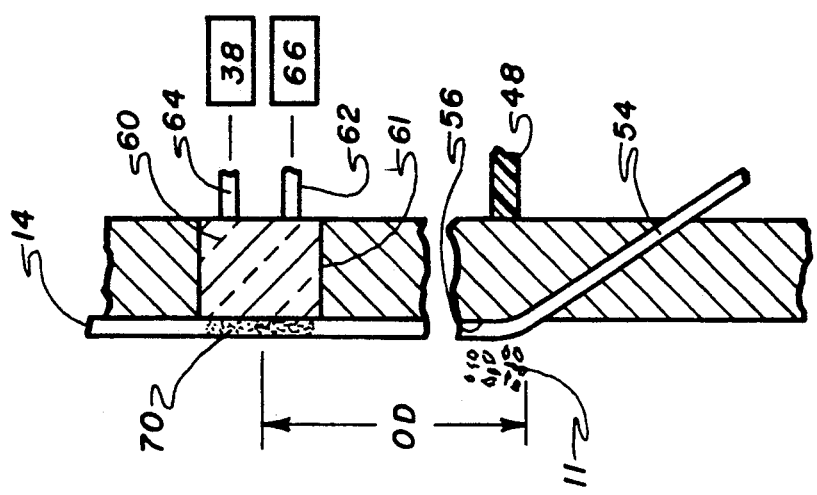
FIG. 3 is a fragmentary side sectional elevation of the tape and penetrometer which has been enlarged for illustrating the operation of the invention.

As the penetrometer 30 moves downwardly in the soil, the optically sensible reaction, e.g. area 70 in FIG. 3, becomes located directly opposite the optical port 60. The excitation fiber 62 couples the light from the source 66 through the optical port 60 to illuminate the fabric portion 16 of the tape. Reflected or fluorescent illumination from the tape is coupled to the measurement fiber 64 and then to the instrument 38.

Figure 4:
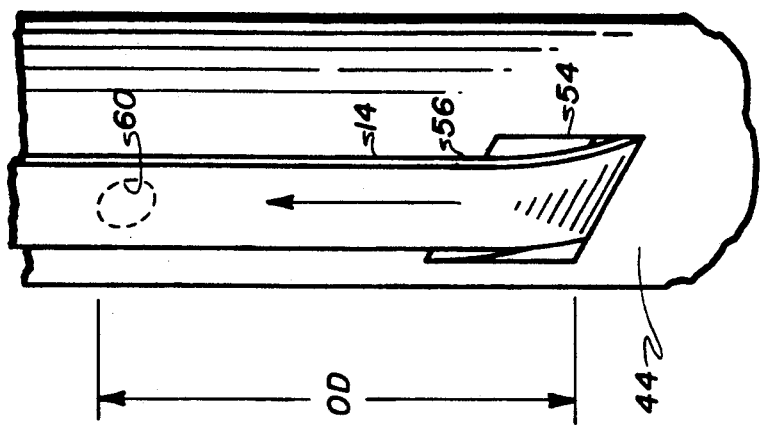
FIG. 4 is a fragmentary perspective of the penetrometer and deployed tape.

In FIGS. 3 and 4 the slot 58 is shown offset from the optical port 60 by an offset distance OD. The time required for the reaction to develop a sensible response in the fabric 16 and the penetration rate can be coordinated so that a continuous scan of the soil sample can be made with each penetrometer push. The rate of penetration is typically about 1 centimeter per second. The slot 54 is located in axially spaced relation with respect to the optical port 60 a sufficient distance, e.g., approximately 10-20 centimeters, so as to allow the contaminants 11 to diffuse into the fabric 16 of the tape 14 and react with the reagent 18 and cause the optically sensible reaction to develop. Of course the rate of penetration may be tailored or altered to whatever appropriate measurement situation is desired.

The invention contemplates a method for producing an in-situ determination of contaminants in soil comprising penetrating the soil with a probe or penetrometer; optically isolating the contaminants with respect to the soil and optically sensing the isolated contaminants. In a particular embodiment, method is implemented by deploying an indicator tape for contacting the soil adjacent of the probe; allowing the indicator tape to react with contaminants in the soil in optical isolation and optically sensing the reaction in the tape. Isolation is achieved in the tape by means of a multilayer structure wherein a reaction zone in the tape is separated from the soil by a diffusion barrier and wherein the soil contaminants diffuse through the barrier into the reaction zone for reaction with a reagent to produce the optically sensible response.

The following examples are presented by way of illustration and should not be construed as limitations on the invention.

EXAMPLE 1

An analytical tape system for measuring the concentration of trinitrotoluene (TNT) in soil is described below. The indicator system for TNT uses the color producing reaction between dissolved TNT and any strongly alkaline aqueous solution, for example, 0.5 normal solution sodium hydroxide, to determine the concentration of TNT in the soil pore water. The indicator tape consists of a white, woven cotton polyester cloth tape that is covered on both sides by a porous plastic membrane formed of a perforated polycarbonate. The plastic membrane can be any material that is inert in sodium hydroxide and that has a pore size that will allow water to contact the tape but will exclude soil particles. In an exemplary embodiment, the porous membrane is a nucleopore membrane manufactured by Costar Corporation of Pleasanton, Calif. The material is a polycarbonate laminate with a 4 micrometer pore size. The spectral signature of the tape can be read through the optical port 60 which comprises a sapphire window using a fiber optic spectrophotometer such as a Guided Wave model 260 manufactured by Guided Wave, Inc., El Dorado Hills, Calif. The concentration of TNT can be estimated by comparing the absorption of the indicator tape with the absorption noted for indicator tapes that have been in contact with soil containing known levels of contamination.

EXAMPLE 2

A fiberoptic spectrophotometer (Guided Wave Model 260) is coupled to 60 feet of 400 micron hardcoated, all silica optical fiber. The system is assembled so that light from a 65 watt tungsten halogen bulb is optically coupled into a fiber and passed through a 30 foot length of 400 micron silica fiber to a sapphire window penetrometer. Light reflected from any medium covering the window is collected in a second fiber and passed through another 30 feet of fiber to the spectrophotometer. A piece of white, cotton polyester, woven, cloth tape, saturated with a color-producing reagent such as a 0.5 normal sodium hydroxide solution, is placed over the sapphire window. The white tape is covered with a porous plastic sheet of polycarbonate laminate membrane perforated with 5 micron diameter holes. A sample of the contaminated soil is prepared by moistening the soil with a saturated aqueous solution of trinitrotoluene (TNT). Isopropyl alcohol (70% solution) is added to the soil at the same time in an amount equal to the amount of water present in the soil. The contaminated soil slurry is packed in a plastic tube and pressed against the back of the porous sheet. Liquid from the contaminated soil moves through the plastic and into the saturated cloth tape. The TNT solution reacts with the sodium hydroxide to form a brownish or reddish stain in the cloth tape. The color change in the tape is measured through the sapphire window using the light source, the fiber optics, and the spectrophotometer. The stain indicates the presence of TNT, and the intensity of the color is related to the concentration of TNT in the solution.

There are many other color-producing reactions that can be used with the method disclosed herein. Additionally, the tape can be used as a medium for fluorometric analyses. If the tape is impregnated with some of the ligands that fluoresce in the presence of specific metals (such as 8-hydroxyquinoline-5-sulfonic acid in the presence of magnesium ion) it should be possible to determine the presence (and the concentration) of theses ions in the soil water by measuring the fluorescence of the tape. Fluorescence quenching can also be used to determine the presence of specific compounds; for example, TNT produces quenching when it comes in contact with some of the polynuclear aromatic compounds. If the fluorophore is impregnated into the tape and the decrease in the fluorescence is measured, the tape can become a very sensitive indicator for specific compounds.

Figure 5:
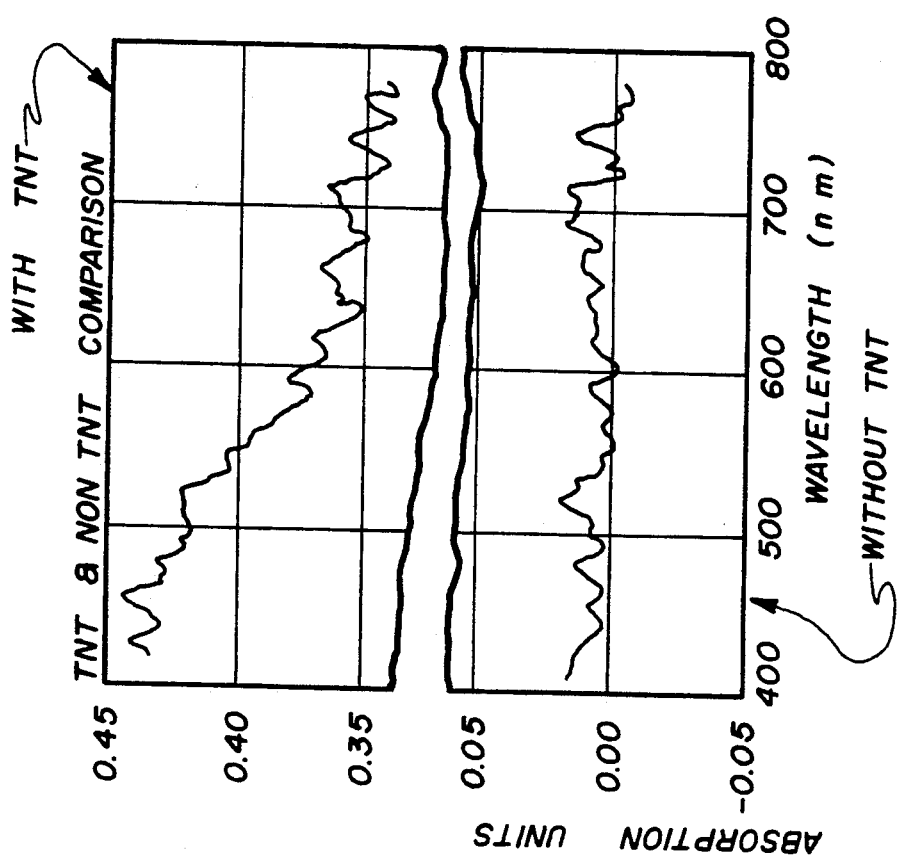
FIG. 5 illustrates comparative spectra showing sensitivity to contaminated soil samples.

FIG. 5 shows spectra collected from contaminated and uncontaminated tape using the exemplary method. As can be seen from the spectra, the absorption is significantly increased in the blue end of the spectrum. The reflected color is reddish brown. The sensed color develops in a few seconds after contact with contaminated soil and persists for about 20-30 minutes. The measurement of the color may be made after 10-20 seconds. Continuous measurements may therefore be made by moving the penetrometer rod at a rate of about 1 cm. per second as the tape makes contact with the soil 10-20 cm. below the optical window.

EXAMPLE 3

"Fluorescence Quenching for the Detection of TNT", by Hurum, von Wandruszka and Grey, in 1991 (Analytical Letters, vol. 24, no. 6, pp 905-911) has demonstrated that the fluorescence in the polynuclear aromatic compound, perylene (dibenz[de, kl]anthracene or peri-dinaphthalene) is quenched by even small amounts of TNT present in solution or as a vapor in air. In order to adapt this quenching reaction for use in detecting TNT in soils in place an indicator tape was prepared that contained a solution of perylene in polyethylene glycol. This solution is a waxy solid that can be placed on the microporous polycarbonate tape. The tape was made to fluoresce by illuminating it with UV light from a nitrogen laser (337 nm wavelength). The tape fluoresces in the blue portion of the spectrum. The intensity of the fluorescence was measured using a EG&G Optical Multichannel Analyzer (EG & G Corp., Princeton, N.J.).

Seventy micrograms of pure (99+%) perylene (Aldrich Chemical Co., Milwaukee, Wis., catalog no. P1, 120-4) were dissolved in 100 ml of high purity methanol. Fifteen grams of polyethylene glycol, average molecular st. 2000 (Aldrich Chemical Co., Milwaukee, Wis., catalog no. 29, 590-6) was added to the methanol/perylene solution. the methanol was permitted to evaporate leaving a semi-solid solution of perylene in polyethylene glycol. The fluorescing solid was spread in a uniform layer on a strip of transparent microporous plastic and placed over the optical port on the cone penetrometer so that the layer could be illuminated with the UV laser. The fluorescence measured over 7000 counts above background. The optical analyzer saturated at 15000 counts. When a drop (0.2 ml) of a 100-ppm solution of TNT in water was placed in contact with the solid the intensity of the fluorescence dropped to background (approximately 200 counts) within 7 to 10 seconds.

The fluorescence quenching reaction can be incorporated into the indicator tape by dispensing an amount of perylene solution in a uniform layer over the transparent plastic tape. The layer containing of perylene solution is then covered with a layer of microporous plastic so that only TNT in a solution or vapor can interact with the solid. The prepared tape can then be placed in the penetrometer and run out against the soil alongside the penetrometer and the fluorescence can be measured using the fluorometer system in the penetrometer. The system has the potential for detecting or measuring the concentrations of TNT in soil gas or soil water down to the low part-per-million or part-per-billion levels.

It is possible to map the contaminated area by making a series of penetrometer pushes and measuring the vertical as well as lateral extent of a TNT-contaminated area.

The present invention permits the in-situ determination by fluorescing a nonfluorescent soil contaminant without requiring that the samples of soil be collected. The invention employs a permeable membrane surrounding a fabric indicator strip that allows the soil water or soil gas to react with compounds in the fabric strip while the soil does not produce a masking color on the indicator. The tape 14 may be retrieved for later analysis. Also, recovery of the tape 14 leaves no significant contamination in the soil as a result of the test.

In accordance with the invention, a procedure for determining changes in the spectral character of the indicator tape uses a remote reading optical instrument, for example, a spectrophotometer, a fluorimeter or a multichannel analyzer coupled to the penetrometer 30 which does not have to be returned to the surface for changes in the optical character of the indicator tape to be measured. The invention also contemplates a procedure for injecting a solvent such as water or water and for example isopropanol into the soil which allows the contaminants to be determined even in profiles containing dry soil layers.

Figure 6:
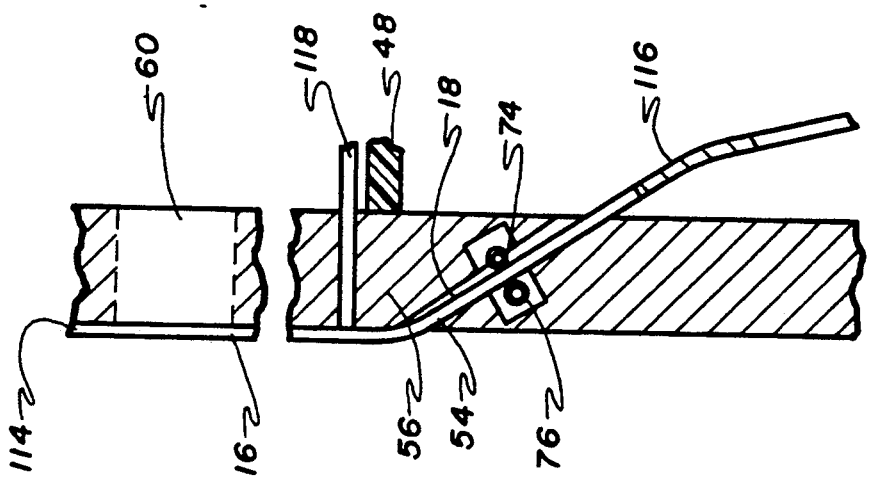
FIG. 6 illustrates an alternative embodiment of the indicator tape; also illustrated is a suction port.

Alternative embodiments include using encapsulated solid or semi-solid reagents 18 in the indicator tape that can be activated by passing the indicator tape between the compression nip 74 of a pair of opposed rollers 76 near the outlet of the slot 54 (FIG. 6). The reagent 18 may be microencapsulated if desired.

The invention also contemplates the use of compounds in the solvent injected into the soil to control variables such as pH or oxidation reduction conditions which could affect color development. Also, one or more control sections of indicator tape may be added that have standard optical characteristics such as color or fluorescence which do not change but permit checks to be made on the operation of the analysis system. For example, in FIG. 6 the tape 114 has a standard length of reagent containing fabric 16 and an intermediate length of fabric containing a standard optically inert material 116. A suction port 118 may be provided in the wall of the penetrometer between the slot 54 and the window 60 to draw compounds through the tape 14 to accelerate diffusion of the contaminants with the reagent saturated fabric 16.

While there has been described what at present are considered to be the preferred embodiments of the present invention, it will be readily apparent to those skilled in the art that various changes and modifications may be made therein without departing from the invention and it is intended in the appended claims to cover such changes and modifications as fall within the true spirit and scope of the invention.

What is claimed is:

1. An apparatus for in-situ determination of soil contamination comprising:
   probe means capable of being inserted into a soil sample;
   means for dispensing a reagent within the probe comprising a means for moving a support tape to contact the soil sample and a reagent carried by the tape that produces an optically measurable reaction with a contaminant in the sample;
   optical means within the probe for measuring the reaction between the sample and the reagent.

2. The apparatus according to claim 1, wherein the probe means comprises a penetrometer having a wall portion and the optical means comprises an optical window formed in the wall.

3. The apparatus according to claim 1, wherein the optically measurable reaction is a change in the reflected spectrum fluorescence or fluorescent quenching.

4. The apparatus according to claim 1, further comprising means within the probe for dispensing a solvent that contacts the sample for facilitating diffusion of the contaminants into the tape.

5. The apparatus according to claim 1, wherein said dispensing means include means for optically isolating the soil from the optical reaction between the sample and the reagent.

6. The apparatus according to claim 5, wherein the means for moving the support tape comprises a pair of pinch rollers for engaging the tape therebetween.

7. The apparatus according to claim 5, wherein the tape has a surface adapted to be located adjacent the optical means and further comprises a diffusion barrier formed on a free surface of the tape in contact with the soil, said diffusion barrier for allowing contaminants to diffuse into the tape for reaction with the reagent.

8. The apparatus according to claim 7, wherein the diffusion barrier comprises a polymeric sheet having micro-pores therein.

9. The apparatus according to claim 8, wherein the polymeric sheet comprises a polycarbonate film.

10. Apparatus for in-situ determination of soil contaminants comprising:
    a penetrometer for penetrating the soil, said penetrometer having an inner chamber, an outer soil contacting wall, an interconnecting tape channel, an optical port in the soil contacting wall and an optical means coupled to the optical port for optical measurements;
    an indicator tape mounted in the inner chamber of the penetrometer, said tape being threaded through the interconnecting tape channel which is positioned and arranged to permit optical measurement of the tape through the optical port;

said tape for carrying a reagent into contact with the soil below the optical port whereby the soil contaminants react with the reagent to develop an optically measurable reaction in the tape at the optical port;

optical means coupled to the optical port for optically sensing said reaction in the tape strip;

sensor means coupled to the optical means responsive to the measured reaction for producing an indication of the reaction for characterizing the contaminant corresponding thereto.

11. The apparatus according to claim 10, wherein the tape comprises a laminate of a reagent carrier and at least one permeable membrane for contact with the soil, said permeable membrane for allowing fluids in the soil to react with the reagent and for blocking optically masking material in the soil from interfering with the optical means.

12. The apparatus of claim 10, further including means for threading a supply of tape into the chamber and through the tape channel.

13. The apparatus according to claim 10, wherein the sensor means comprises a spectrophotometer, a fluorimeter, or a multichannel analyzer.

14. The apparatus of claim 10, further comprising pinch roller means having a set of compression rollers therebetween located at the tape channel, said pinch roller means for capturing the tape therebetween.

15. The apparatus of claim 10, wherein the permeable membrane is transparent to excitation and responsive radiation.

16. A method for in-situ determination of soil contaminants comprising:
placing a probe within the soil sample that contacts the soil with a reagent carrying medium to create an optically measurable reaction between the contaminants and the reagent;
optically shielding the medium from the soil except at a position having an optical port through which the reaction can be measured;
measuring the reaction to determine the presence of the contaminants.

17. A method for in-situ determination of soil contaminants comprising:
placing a probe within the soil sample, the probe comprises, a support tape to contact the soil sample and a reagent carried by the tape that produces an optically measurable reaction with a contaminant in the sample;
optically shielding the medium from the soil except at a position having an optical port through which the reaction can be measured;
measuring the reaction to determine the presence of the contaminants.

* * * * *